US010448899B2

(12) United States Patent
Thakur et al.

(10) Patent No.: US 10,448,899 B2
(45) Date of Patent: Oct. 22, 2019

(54) PREDICTION OF WORSENING OF HEART FAILURE USING BLENDED REFERENCE

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Viktoria A. Averina, Shoreview, MN (US); John D. Hatlestad, Maplewood, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 271 days.

(21) Appl. No.: 15/335,754

(22) Filed: Oct. 27, 2016

(65) Prior Publication Data

US 2017/0119317 A1    May 4, 2017

Related U.S. Application Data

(60) Provisional application No. 62/247,995, filed on Oct. 29, 2015.

(51) Int. Cl.
*A61B 5/00* (2006.01)
*G16H 50/30* (2018.01)
(Continued)

(52) U.S. Cl.
CPC ............. *A61B 5/7275* (2013.01); *A61B 5/02* (2013.01); *A61B 5/02028* (2013.01);
(Continued)

(58) Field of Classification Search
CPC ..... A61B 5/7275; A61B 5/02; A61B 5/04004; A61B 5/053; A61B 5/0535; A61B 5/686;
(Continued)

(56) References Cited

U.S. PATENT DOCUMENTS

| 5,213,098 A | 5/1993 | Bennett et al. |
| 5,269,301 A | 12/1993 | Cohen |

(Continued)

FOREIGN PATENT DOCUMENTS

| CN | 108366729 A | 8/2018 |
| WO | WO-2015065674 A1 | 5/2015 |
| WO | WO-2017075154 A1 | 5/2017 |

OTHER PUBLICATIONS

"International Application Serial No. PCT/US2016/059020, International Preliminary Report on Patentability dated May 11, 2018", 10 pgs.

(Continued)

*Primary Examiner* — Paula J Stice
(74) *Attorney, Agent, or Firm* — Schwegman Lundberg & Woessner, P.A.

(57) ABSTRACT

Systems and methods for detecting cardiac conditions such as events indicative of worsening of heart failure (HF) are described. A system can receive a physiological signal from a patient, transform one or more first portions of the physiological signal into respective one or more baseline statistical values, transform one or more second portions of the physiological signal into one or more historical extreme values, and generate one or more reference values of a physiologic parameter using the baseline statistical values and the historical extreme values. The system can transform one or more third signal portions of the physiological signal into respective one or more short-term values, and produce a cardiac condition indicator using a combination of relative differences between the short-term values and the corresponding reference values. The system can output the cardiac condition indicator, or deliver therapy according to the cardiac condition indicator.

20 Claims, 6 Drawing Sheets

(51) Int. Cl.

| | |
|---|---|
| *A61B 8/08* | (2006.01) |
| *A61B 5/02* | (2006.01) |
| *A61B 5/053* | (2006.01) |
| *A61B 5/04* | (2006.01) |
| *A61B 7/04* | (2006.01) |
| *A61B 7/00* | (2006.01) |
| *A61B 7/02* | (2006.01) |
| *G16H 40/63* | (2018.01) |
| *G16H 50/20* | (2018.01) |
| *A61B 5/11* | (2006.01) |

(52) U.S. Cl.
CPC .......... *A61B 5/04004* (2013.01); *A61B 5/053* (2013.01); *A61B 5/0535* (2013.01); *A61B 5/4836* (2013.01); *A61B 5/4842* (2013.01); *A61B 5/686* (2013.01); *A61B 5/7225* (2013.01); *A61B 5/7282* (2013.01); *A61B 7/00* (2013.01); *A61B 7/023* (2013.01); *A61B 7/04* (2013.01); *A61B 8/0883* (2013.01); *G16H 40/63* (2018.01); *G16H 50/20* (2018.01); *G16H 50/30* (2018.01); *A61B 5/1102* (2013.01); *A61B 2505/07* (2013.01)

(58) Field of Classification Search
CPC .... A61B 5/7252; A61B 5/0883; G16H 50/30; G16H 50/20
See application file for complete search history.

(56) References Cited

U.S. PATENT DOCUMENTS

| | | | |
|---|---|---|---|
| 5,330,505 A | 7/1994 | Cohen | |
| 5,402,794 A | 4/1995 | Wahlstrand et al. | |
| 5,782,890 A | 7/1998 | Wahlstrand et al. | |
| 5,794,615 A | 8/1998 | Estes | |
| 5,876,353 A | 3/1999 | Riff | |
| 5,957,861 A | 9/1999 | Combs et al. | |
| 5,964,788 A | 10/1999 | Greenhut | |
| 6,105,575 A | 8/2000 | Estes et al. | |
| 6,512,949 B1 | 1/2003 | Combs et al. | |
| 6,609,517 B1 | 8/2003 | Estes et al. | |
| 6,636,762 B2 | 10/2003 | Begemann | |
| 6,829,503 B2 | 12/2004 | Alt | |
| 6,904,320 B2 | 6/2005 | Park et al. | |
| 6,932,084 B2 | 8/2005 | Estes et al. | |
| 6,970,742 B2 | 11/2005 | Mann et al. | |
| 7,296,573 B2 | 11/2007 | Estes et al. | |
| 7,329,226 B1 | 2/2008 | Ni et al. | |
| 7,363,085 B1 | 4/2008 | Benser et al. | |
| 7,430,447 B2 | 9/2008 | Min et al. | |
| 7,483,743 B2 | 1/2009 | Mann et al. | |
| 7,488,291 B2 | 2/2009 | Cho et al. | |
| 7,519,425 B2 | 4/2009 | Benser et al. | |
| 7,590,449 B2 | 9/2009 | Mann et al. | |
| 7,616,991 B2 | 11/2009 | Mann et al. | |
| 7,628,757 B1 | 12/2009 | Koh | |
| 7,717,110 B2 | 5/2010 | Kane et al. | |
| 7,717,854 B2 | 5/2010 | Mann et al. | |
| 7,810,496 B2 | 10/2010 | Estes | |
| 7,837,629 B2 | 11/2010 | Bardy | |
| 7,937,137 B2 | 5/2011 | Cho et al. | |
| 7,963,922 B2 | 6/2011 | Taepke, II et al. | |
| 7,972,276 B1 | 7/2011 | Min | |
| 7,988,635 B2 | 8/2011 | Cho et al. | |
| 8,073,541 B2 | 12/2011 | Alt et al. | |
| 8,160,702 B2 | 4/2012 | Mann et al. | |
| 8,220,456 B2 | 7/2012 | Kane et al. | |
| 8,226,570 B2 | 7/2012 | Yachuan et al. | |
| 8,282,562 B2 | 10/2012 | Koh | |
| 8,295,918 B2 | 10/2012 | Rosenberg et al. | |
| 8,308,650 B2 | 11/2012 | Bardy | |
| 8,359,093 B2 | 1/2013 | Wariar | |
| 8,380,303 B2 | 2/2013 | Rosenberg | |
| 8,428,698 B2 | 4/2013 | Keel et al. | |
| 8,437,837 B2 | 5/2013 | Zhou | |
| 8,442,627 B2 | 5/2013 | Hess | |
| 8,457,743 B2 | 6/2013 | Gollasch | |
| 8,483,821 B2 | 7/2013 | Averina et al. | |
| 8,551,010 B2 | 10/2013 | Pu et al. | |
| 8,554,315 B2 | 10/2013 | Cho et al. | |
| 8,634,906 B2 | 1/2014 | Wariar | |
| 8,695,595 B2 | 4/2014 | Kane et al. | |
| 8,700,143 B2 | 4/2014 | Stylos | |
| 8,777,851 B2 | 7/2014 | Alt | |
| 8,795,189 B2 | 8/2014 | Ni | |
| 8,882,684 B2 | 11/2014 | Halperin et al. | |
| 8,998,830 B2 | 4/2015 | Halperin et al. | |
| 2010/0073170 A1 | 3/2010 | Siejko et al. | |
| 2011/0245711 A1 | 10/2011 | Katra et al. | |
| 2011/0301491 A1 | 12/2011 | Stadler et al. | |
| 2012/0157864 A1 | 6/2012 | Thakur et al. | |
| 2012/0158079 A1 | 6/2012 | Rosenberg et al. | |
| 2014/0236026 A1 | 8/2014 | Zhang et al. | |
| 2014/0296726 A1 | 10/2014 | Brockway et al. | |
| 2014/0323846 A1 | 10/2014 | Niebel et al. | |
| 2015/0157273 A1 | 6/2015 | An et al. | |
| 2017/0119317 A1 | 5/2017 | Thakur et al. | |

OTHER PUBLICATIONS

"International Application Serial No. PCT/US2016/059020, International Search Report dated Feb. 2, 2017", 4 pgs.
"International Application Serial No. PCT/US2016/059020, Written Opinion dated Feb. 2, 2017", 8 pgs.

US 10,448,899 B2

PREDICTION OF WORSENING OF HEART FAILURE USING BLENDED REFERENCE

CLAIM OF PRIORITY

This application claims the benefit of priority under 35 U.S.C. § 119(e) of U.S. Provisional Patent Application Ser. No. 62/247,995, filed on Oct. 29, 2015, which is herein incorporated by reference in its entirety.

TECHNICAL FIELD

This document relates generally to medical devices, and more particularly, to systems, devices and methods for detecting and monitoring events indicative of worsening of congestive heart failure.

BACKGROUND

Congestive heart failure (CHF or HF) is a major health problem and affects many people in the United States alone. CHF patients can have enlarged heart with weakened cardiac muscles, resulting in poor cardiac output of blood. Although CHF is usually a chronic condition, it can occur suddenly. It can affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

In many CHF patients, elevated pulmonary vascular pressures can cause fluid accumulation in the lungs over time. The fluid accumulation can precede or coincide with worsening HF such as episodes of HF decompensation. The HF decompensation can be characterized by pulmonary or peripheral edema, reduced cardiac output, and symptoms such as fatigue, shortness of breath, and the like.

OVERVIEW

Frequent monitoring of CHF patients and timely detection of thoracic fluid accumulation or other events indicative of HF decompensation status can help prevent worsening HF in CHF patients, hence reducing cost associated with HF hospitalization. Additionally, identification of patient at an elevated risk of developing future events of worsening HF can help ensure timely treatment, thereby improving the prognosis and patient outcome. Identifying and safely managing the patients having risk of future HF events can avoid unnecessary medical intervention and reduce healthcare cost.

Ambulatory medical devices (AMIDs) can be used for monitoring HF patient and detecting HF decompensation events. Examples of such AMDs can include implantable medical devices (IMD), subcutaneous medical devices, wearable medical devices or other external medical devices. The AMDs can include, or be communicatively coupled to, physiologic sensors which can be configured to sense electrical activity and mechanical function of the heart. The AMDs can deliver therapy such as electrical stimulations to target tissues or organs, such as to restore or improve the cardiac function. Some of these devices can provide diagnostic features, such as using transthoracic impedance or other sensor signals to detect a disease or a disease condition. For example, fluid accumulation in the lungs decreases the transthoracic impedance due to the lower resistivity of the fluid than air in the lungs. Fluid accumulation in the lungs can also irritate the pulmonary system and leads to decrease in tidal volume and increase in respiratory rate.

Prediction of a future HF decompensation event, such as by detecting a precipitating event such as increased thoracic fluid accumulation, can be based on a detected change of a sensor signal (such as a thoracic impedance signal) from a reference signal. Detection of an event precipitating HF decompensation may be affected by a number of factors including the choice of physiologic sensors or physiological signals. For example, a detector using a physiologic sensor may provide desirable accuracy in HF decompensation event detection in one patient but less sensitive or less specific in another patient. The performance of a detector using a particular sensor signal may change over time such as due to patient's disease progression, development of a new medical condition, or other confounding factors attributed to patient's physiologic responses or environmental noise.

Techniques such as signal filtering or smoothing can be used to produce a less noisy reference sensor signal, such that a change of the sensor signal from the reference signal can be more reliably predictive of future HF decompensation events. However, signal filtering or smoothing may not be effective in some circumstances, and may not yield reliable and accurate detection of HF decompensation, such as when the confounding events or the noise interferences cause long and sustained changes of sensor signal in a direction (which is also known as signal drift over time). A reference signal that is generated using signal smoothing, such as over a "data-smoothing window", can be disproportionally affected more by the data characteristics within the data-smoothing window than by the patient's historical data. The historical sensor data, associated with patient disease progression and treatment history, can provide a benchmark of patient health status. Because the data-smoothing based reference signal may not preserve the power of the historical sensor data in recognizing the presence or non-occurrence of the target event (e.g., a HF decompensation event), undesirably low sensitivity to detection of worsening HF or inappropriate detection of a termination of a worsened HF status (or, a detection of improvement of HF status) may result. At least with these issues in consideration, the present inventors have recognized that there remains a considerable need for improving HF decompensation detection in CHF patients using multiple sensors.

This document discusses, among other things, systems and methods for detecting cardiac conditions such as events indicative of worsening HF. A system can include a signal input circuit to sense a physiological signal from a patient, transform one or more first portions of the physiological signal into respective one or more baseline statistical values, transform one or more second portions of the physiological signal into one or more historical extreme values, and generate one or more reference values of a physiologic parameter using the baseline statistical values and the historical extreme values. The system can transform one or more third signal portions of the physiological signal into respective one or more short-term values, and produce a cardiac condition indicator using a combination of relative differences between the short-term values and the corresponding reference values. The system can output the cardiac condition indicator, or deliver therapy according to the cardiac condition indicator.

In Example 1, a system can comprise a signal input circuit, a memory circuit, a reference value generator circuit, a short-term value generator circuit, a cardiac condition detector circuit, and an output unit. The signal input circuit can include a sense amplifier circuit to sense at least one physiological signal from a patient. The reference value generator circuit can be coupled to the signal input circuit and the memory circuit, and include a filter circuit to transform one or more first signal portions of the received at least one physiological signal during respective one or more first time windows into respective one or more baseline statistical values, a comparator circuit to transform one or more second signal portions of the received at least one physiological signal during respective one or more second time windows into respective one or more historical extreme values, and a blending circuit to generate one or more reference values of a physiologic parameter stored in the memory circuit using the respective one or more baseline statistical values and the respective one or more historical extreme values. The short-term value generator circuit can be coupled to the signal input circuit and the memory circuit to transform one or more third signal portions of the received at least one physiological signal during respective one or more third time windows into respective one or more short-term values stored in the memory circuit. The one or more third time windows shorter than the respective first and second time windows. The cardiac condition detector circuit can be coupled to the memory circuit or to the reference value generator circuit and short-term value generator circuits to determine a cardiac condition indicator using the one or more short-term values and the one or more reference values. The output unit can generate a human-perceptible presentation of an indication of a progression over time of the cardiac condition indicator.

Example 2 can include, or can optionally be combined with the subject matter of Example 1 to optionally include, the filter circuit that can produce the baseline statistical values including respective statistical measures of the physiologic parameter using the respective one or more first signal portions. The comparator circuit can produce the one or more historical extreme values including respective one or more maxima or minima of the physiologic parameter using the respective one or more second signal portions.

Example 3 can include, or can optionally be combined with the subject matter of one or any combination of Examples 1 or 2 to include, the blending circuit that can generate the one or more reference values using a linear or a nonlinear combination of at least one of the one or more baseline statistical values and at least one of the one or more historical extreme values.

Example 4 can include, or can optionally be combined with the subject matter of one or any combination of Examples 1 through 3 to include, the one or more first time windows that are different from the respective one or more second time windows by at least one of a window start time, a window end time, or a window duration.

Example 5 can include, or can optionally be combined with the subject matter of Example 4 to optionally include, at least one of the one or more second time windows that precedes the corresponding first time window in time.

Example 6 can include, or can optionally be combined with the subject matter of one or any combination of Examples 4 or 5 to include, at least one of the one or more second time windows that has a longer window duration than the corresponding first time window.

Example 7 can include, or can optionally be combined with the subject matter of one or any combination of Examples 1 through 6 to include, the signal input circuit that can sense a heart sound (HS) signal, the filter circuit that can generate the one or more baseline statistical values including central tendency of S3 heart sound intensity values using one or more first signal portions of the received HS signal, and the comparator circuit that can generate the one or more historical extreme values including minimal S3 heart sound intensity values using one or more second signal portions of the received HS signal.

Example 8 can include, or can optionally be combined with the subject matter of one or any combination of Examples 1 through 6 to include, the signal input circuit that can sense the at least one physiologic signal including an impedance (Z) signal, the filter circuit that can generate the one or more baseline statistical values including central tendency of Z values using one or more first signal portions of the received Z signal, and the comparator circuit that can generate the one or more historical extreme values including maximal Z values using one or more second signal portions of the received Z signal.

Example 9 can include, or can optionally be combined with the subject matter of one or any combination of Examples 1 through 8 to include, the reference value generator circuit that can update the one or more baseline statistical values using respective one or more specified portions of the received at least one physiologic signal. The one or more specified portions postdate the corresponding one or more first time windows.

Example 10 can include, or can optionally be combined with the subject matter of one or any combination of Examples 1 through 9 to include, the reference value generator circuit that can update the one or more historical extreme values using respective one or more updated second time windows. The one or more updated second time windows can be different from the corresponding second time windows by at least one of a window start time, a window end time, or a window duration.

Example 11 can include, or can optionally be combined with the subject matter of one or any combination of Examples 1 through 10 to include, the short-term value generator circuit that can generate the one or more short-term values using a statistical measure of the respective one or more third signal portions of the received at least one physiological signal.

Example 12 can include, or can optionally be combined with the subject matter of one or any combination of Examples 1 through 11 to include, the cardiac condition detector circuit that can determine the cardiac condition indicator using a combination of differences between the one or more short-term values and the corresponding one or more reference values, where each of the differences is scaled by a specified weight factor.

Example 13 can include, or can optionally be combined with the subject matter of one or any combination of Examples 1 through 12 to include, the cardiac condition detector circuit that can determine the cardiac condition indicator including an indicator of a future heart failure (HF) decompensation event.

Example 14 can include, or can optionally be combined with the subject matter of one or any combination of Examples 1 through 13 to include, the cardiac condition detector circuit that can detect an onset of a cardiac condition when a cardiac condition indicator meets a first criterion, and a termination of the cardiac condition when the cardiac condition indicator meets a second criterion.

Example 15 can include, or can optionally be combined with the subject matter of one or any combination of Examples 1 through 14 to include, a therapy circuit configured to deliver a therapy to the patient in response to the cardiac condition indicator meeting a specified condition.

In Example 16, a method can include steps of receiving at least one physiological signal sensed from a patient, transforming one or more first signal portions of the received at least one physiological signal during respective one or more first time windows into respective one or more baseline statistical values, and transforming one or more second signal portions of the received at least one physiological signal during respective one or more second time windows into respective one or more historical extreme values. The method can include generating one or more reference values of a physiologic parameter stored in the memory circuit using the respective one or more baseline statistical values and the respective one or more historical extreme values, and transforming one or more third signal portions of the received at least one physiological signal during respective one or more third time windows into respective one or more short-term values stored in the memory circuit. The one or more third time windows can be shorter than the respective first and second time windows. The method can include determining a cardiac condition indicator using the one or more short-term values and the one or more reference values, and generating a human-perceptible presentation of an indication of a progression over time of the cardiac condition indicator.

Example 17 can include, or can optionally be combined with the subject matter of Example 16 to optionally include, generating the one or more baseline statistical values including respective statistical measures of the physiologic parameter using the respective one or more first signal portions, and the one or more historical extreme values including respective one or more maxima or minima of the physiologic parameter using the respective one or more second signal portions.

Example 18 can include, or can optionally be combined with the subject matter of Example 16 to optionally include, the one or more first time windows used for generating the baseline statistical values to be different from the respective one or more second time windows for generating the historical extreme values by at least one of a window start time, a window end time, or a window duration.

Example 19 can include, or can optionally be combined with the subject matter of Example 16 to optionally include, receiving the at least one physiological signal including a heart sound (HS) signal, computing central tendency of S3 heart sound intensity values using one or more first signal portions of the received HS signal, and identifying one or more minimal S3 heart sound intensity values from respective one or more second signal portions of the received HS signal.

Example 20 can include, or can optionally be combined with the subject matter of Example 16 to optionally include, receiving the at least one physiological signal including an impedance (Z) signal, computing central tendency of Z values using one or more first signal portions of the received Z signal, and identifying one or more maximal Z values from respective one or more second signal portions of the received Z signal.

Example 21 can include, or can optionally be combined with the subject matter of Example 16 to optionally include, updating the one or more baseline statistical values or updating the one or more historical extreme values. The baseline statistical values can be updated using respective one or more specified portions of the received physiologic signal, where the one or more specified portions can postdate the corresponding one or more first time windows. The historical extreme values can be updated using respective one or more updated second time windows. The updated second time windows can differ from the corresponding second time windows by at least one of a window start time, a window end time, or a window duration.

Example 22 can include, or can optionally be combined with the subject matter of Example 16 to optionally include, determining the cardiac condition indicator including a combination of differences between the one or more short-term values and the corresponding one or more reference values, where each of the differences is scaled by a specified weight factor.

Example 23 can include, or can optionally be combined with the subject matter of Example 16 to optionally include, delivering a therapy to the patient in response to the cardiac condition indicator meeting a specified condition.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting one or more target physiologic events or conditions. The events can include early precursors of a HF decompensation episode. That is, these events can occur well before the systematic manifestation of worsening HF. Therefore, by detecting the precursor events, the present subject matter can provide a method and device for detecting an impending HF decompensation episode. The systems, devices, and methods described herein may be used to determine cardiac condition such as HF status and/or track progression of the cardiac condition such as worsening of or recovery from a HF event. This system can also be used in the context of other diseases associated with accumulation of thoracic fluid, such as pneumonia.

Figure 1:
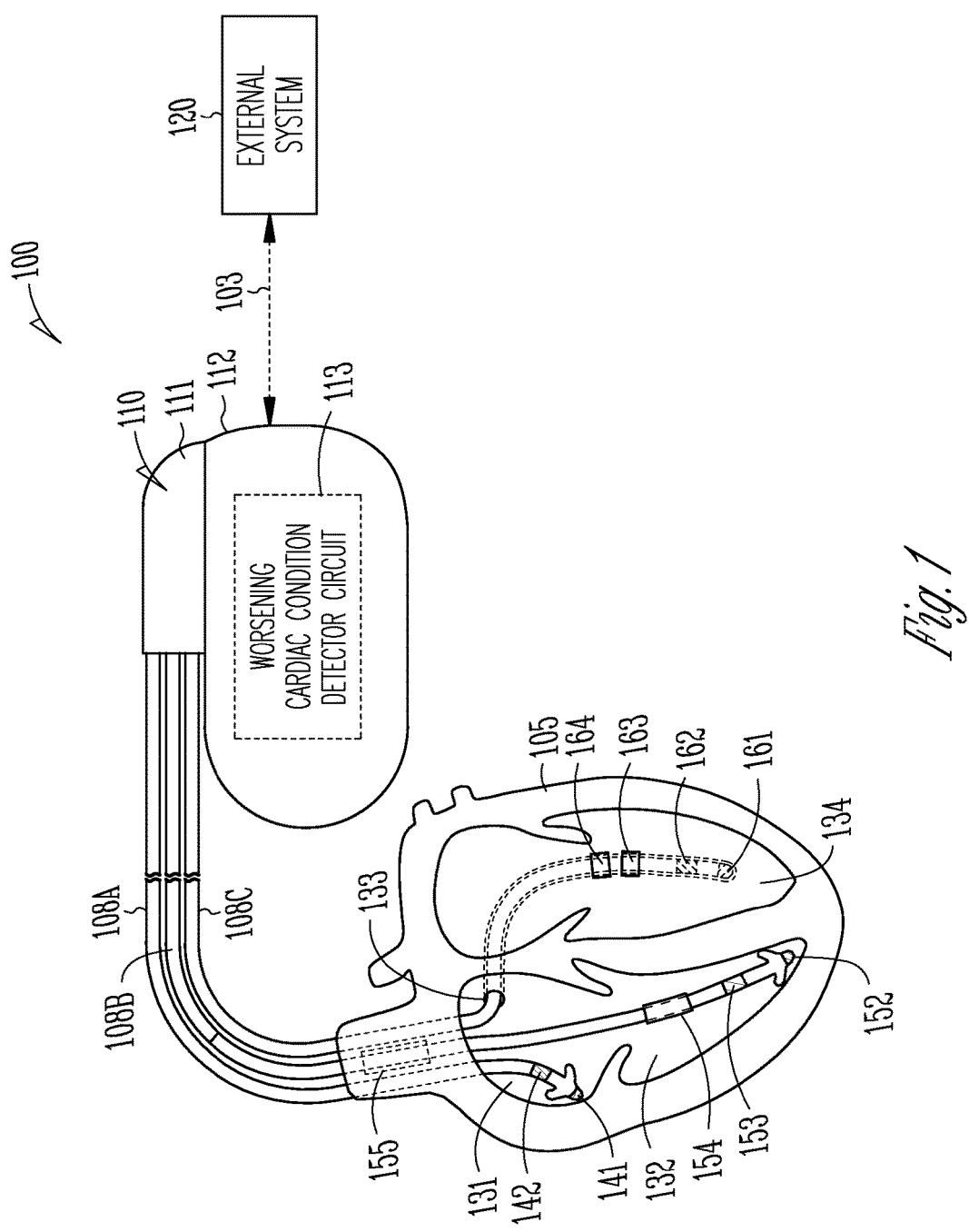
FIG. 1 illustrates generally an example of a cardiac rhythm management (CRM) system and portions of the environment in which the CRM system operates.

FIG. 1 illustrates generally an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as an implantable diagnostic device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can housing 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can housing 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 can sense impedance such as between electrodes located on one or more of the leads 108A-C or the can housing 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiological signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of thoracic or transthoracic impedance, intracardiac impedance, arterial pressure, pulmonary artery pressure, RV pressure, LV coronary pressure, coronary blood temperature, blood oxygen saturation, one or more heart sounds, physical activity or exertion level, arrhythmias, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are contemplated.

As illustrated, the CRM system 100 can include a worsening cardiac condition detector 113. The worsening cardiac condition detector 113 can receive a physiological signal, such as sensed from the patient using the electrodes on one or more of the leads 108A-C or the can housing 112, or other physiologic sensors deployed on or within the patient and communicated with the IMD 110. Examples of the physiological signals can include thoracic impedance signal, heart sounds signal, cardiac pressure signals, respiration signals, among others. The worsening cardiac condition detector 113 can determine one or more baseline statistical values and one or more historical extreme values of a physiological parameter using respectively specified signal portions of the physiological signal, and generate one or more composite reference values using the baseline statistical values and the respective historical extreme values. The worsening cardiac condition detector 113 can transform one or more portions of the physiological signal into respective one or more short-term values, and calculate deviations of the short-term values away from the composite reference values of the physiological signal, and detect a cardiac condition such as a worsening HF event from the patient. The worsening HF event can include one or more early precursors of a HF decompensation episode, or an event indicative of HF progression such as deterioration of HF status. The worsening cardiac condition detector 113 can also be modified to detect recovery of HF status, or other physiologic events such as pulmonary edema, pneumonia, or myocardial infarction, among others. Examples of the worsening cardiac condition detector 113 are described below, such as with reference to FIGS. 2-3.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The worsening cardiac condition detector 113 may be implemented in the external system 120. The external system 120 can be configured to perform HF decompensation event detection such as using data extracted from the IMD 110 or data stored in a memory within the external system 120. Portions of the worsening cardiac condition detector 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

While described with reference to the IMD 110, the CRM system 100 can include a subcutaneous medical device (e.g., subcutaneous pacemaker or ICD, a subcutaneous monitor, or a subcutaneous diagnostic device), a wearable medical device (e.g., a patch based sensing device), or other external medical devices for medical diagnostics or therapy using various energy sources (e.g., electrical, electromagnetic, optical, or mechanical) or therapeutic agents. The subcutaneous, wearable, or external medical device can be an untethered device that needs not be tethered to an electrode or another device by a leadwire or other wired connection (such as one of the leads 108A-C). The untethered device can include one or more electrodes on a can housing of the device, or wirelessly communicate with a sensor or another device associated with the patient.

Figure 2:
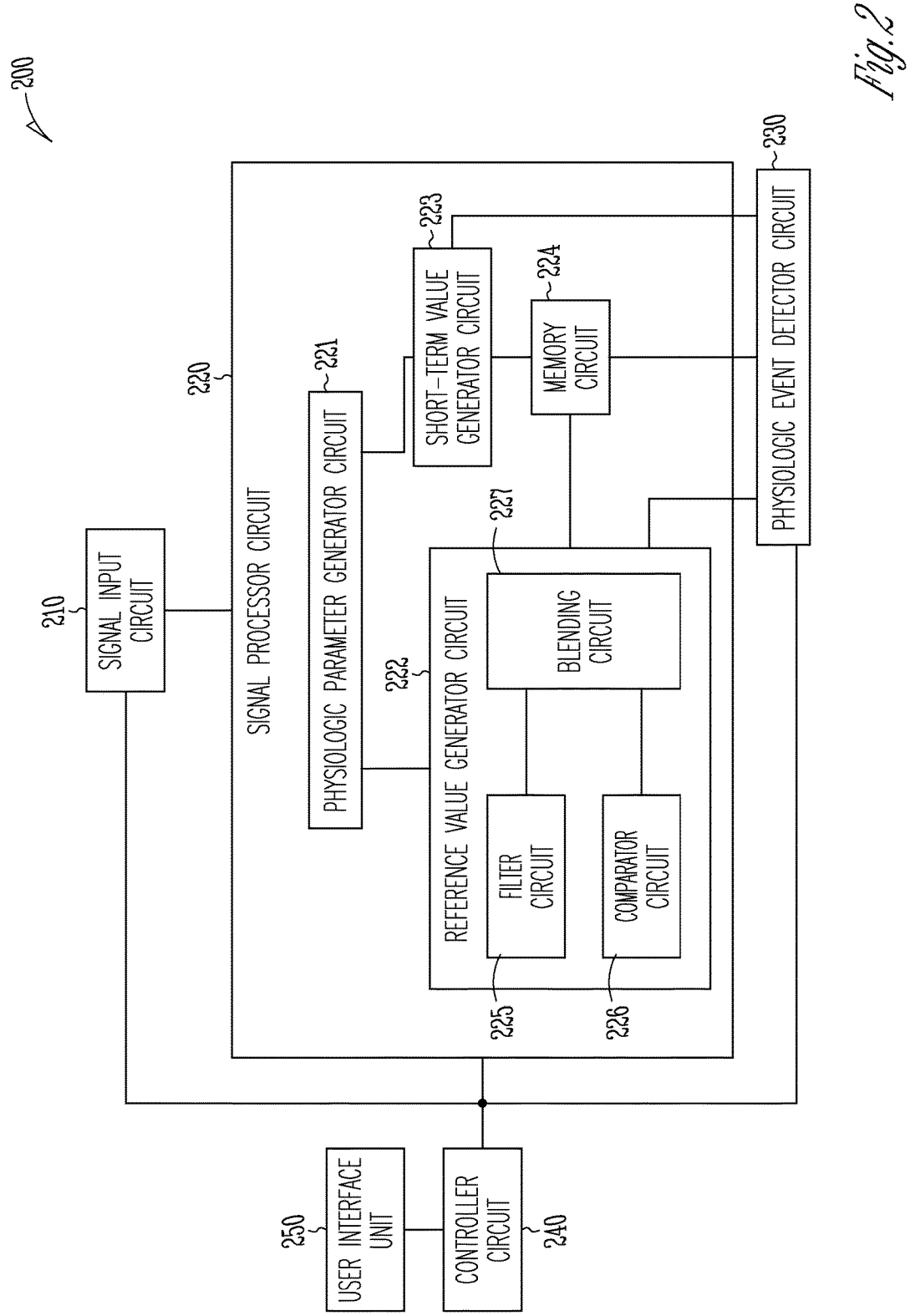
FIG. 2 illustrates generally an example of a target physiologic event detector for detecting an event such as a target cardiac condition.

FIG. 2 illustrates generally an example of a target physiologic event detector 200 that can be configured to detect a target physiologic event from a patient, such as a worsening HF event or other cardiac conditions. The target physiologic event detector 200 can be an embodiment of the worsening cardiac condition detector 113, and configured to detect worsening HF using at least one physiological signal sensed from the patient. The target physiologic event detector 200 can include one or more of a signal input circuit 210, a signal processor circuit 220, a physiologic event detector circuit 230, a controller circuit 240, and a user interface unit 250.

The signal input circuit 210 can include a sense amplifier circuit to sense a physiological signal sensed from a patient, such as a physiological signal containing information indicative of status or progression of HF. In an example, the sense amplifier circuit can be coupled to one or more electrodes such as the electrodes on one or more of the leads 108A-C or the can housing 112, one or more implantable, wearable, or other ambulatory sensors, or one or more patient monitors. The signal input circuit 210 can include one or more other sub-circuits to digitize, filter, or perform other signal conditioning operations on the received physiological signal. In an example, the signal input circuit 210 can receive one or more physiological signals from a storage device such as an electronic medical record (EMR) system, such as in response to a command signal provided by a system user.

In an example, the signal input circuit 210 can be coupled to one or more electrodes on one or more of the leads 108A-C or the can housing 112 to measure an impedance (Z) signal from a patient. The impedance can include a plurality of measurements of thoracic impedance or cardiac impedance. The impedance can be produced by injecting current between a first pair of electrodes and sensing the resultant voltage across a second pair of electrodes. For example, the impedance can be sensed across an RA electrode 141 or 142 and the can housing 112 ($Z_{RA-Can}$), across an RV electrode 152, 153 or 154 and a can housing 112 ($Z_{RV-Can}$), or across an LV electrode selected from electrodes 161-164 and the can housing 112 ($Z_{RV-Can}$). The impedance can include an impedance vector where the voltage sensing electrodes are the currently injection electrodes are orthogonal to each other, such as selected from RA, RV, or LV electrodes ($Z_{RA-RV-LV}$).

In another example, the signal input circuit 210 can be coupled to at least one heart sound (HS) sensor to sense a HS signal from the patient. The HS sensor can be an implantable, wearable, or otherwise ambulatory sensor, and placed external to the patient or implanted inside the body. Examples of the HS sensors can include an accelerometer, an acoustic sensor, a microphone, a piezo-based sensor, or other vibrational or acoustic sensors can also be used to sense the HS signal. The signal input circuit 210 can alternatively or additionally receive one or more of electrocardiograph (ECG) or electrograms (EGM), a pulmonary artery pressure signal, an RV pressure signal, an LV coronary pressure signal, a coronary blood temperature signal, a blood oxygen saturation signal, or a respiration signal rate signal or a tidal volume signal, among others.

The signal processor circuit 220, coupled to the signal input circuit 210, can generate characteristic values from the received signal for use in detecting a target cardiac condition such as a worsening HF event. In an example, the signal processor circuit 220 can be implemented as a part of a microprocessor circuit. The microprocessor circuit can be a dedicated processor such as a digital signal processor, application specific integrated circuit (ASIC), microprocessor, or other type of processor for processing information including the physiological signals received from the signal input circuit 210. Alternatively, the microprocessor circuit can be a general purpose processor that can receive and execute a set of instructions of performing the functions, methods, or techniques described herein.

In an example such as illustrated in FIG. 2, the signal processor circuit 220 can include circuit sets comprising one or more other circuits or sub-circuits, including a physiologic parameter generator circuit 221, a reference value generator circuit 222, a short-term value generator circuit 223, and a memory circuit 224. The subcircuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The physiologic parameter generator circuit 221 can extract from the sensed physiological signal one or more signal parameters, including signal mean, median, or other central tendency measures, a histogram of the signal intensity, or one or more signal trends over time. In an example, the physiologic parameter generator circuit 221 can generate a composite signal parameter set such as using the two or more physiological signals. Examples of the physiologic parameters can include cardiac or thoracic impedance, intensity or timing of a HS component such as S1, S2, S3 or S4 heart sound, heart rate, respiration rate, respiration pattern descriptors such as apnea index indicating the frequency of sleep apnea, hypopnea index indicating the frequency of sleep hypopnea, apnea-hypopnea index (AHI) indicating the frequency of or sleep hypopnea events, or a rapid shallow breathing index (RSBI) which can be computed as a ratio of respiratory frequency (number of breaths per minutes) to tidal volume, among others.

In an example, the signal input circuit 210 can receive a thoracic or cardiac impedance signal according to a specified impedance sensing configuration, and the physiologic parameter generator circuit 221 can generate impedance parameters using specified portions of the received impedance signal, such as during specified time or during the occurrence of specified physiologic events. For example, the physiologic parameter generator circuit 221 can generate the impedance parameters using portions of the received impedance signal during identical phases of a cardiac cycle (such as within a certain time window relative to R-wave), or at identical phases of a respiratory cycle (such as within the inspiration phase, or the expiration phase). This may minimize or attenuate the interferences such as due to cardiac or respiratory activities, in the impedance measurements.

The physiologic parameter generator circuit 221 can generate a trend of physiologic parameters using impedance measurements collected during one or more impedance acquisition and analysis sessions. In an example, an impedance acquisition and analysis session can start between approximately 5 a.m. and 9 a.m. in the morning, and lasts for approximately 2-8 hours. In another example, the impedance acquisition and analysis session can be programmed to exclude certain time periods, such as night time, or when the patient is asleep. The impedance parameter can be determined as a median of multiple impedance measurements acquired during the impedance acquisition and analysis session. The resultant multiple impedance parameter values can be used by the reference value generator circuit 222 and the short-term value generator circuit 223 to generate respective characteristic impedance values. In some examples, the physiologic parameter generator circuit 221 can sense two or more physiological signals such as according to two or more impedance sensing vectors, and can generate a composite impedance parameter using the two or more physiological signals.

The reference value generator circuit 222 can include a filter circuit 225, a comparator circuit 226, and a blending circuit 227. The filter circuit 225 can transform one or more first signal portions of the received physiological signal during respective one or more first time windows ($W_{L1}$) into respective one or more baseline statistical values ($X_{BL}$). The baseline statistical values can include statistical measures of a physiologic parameter using the respective one or more first signal portions during the first time windows $W_{L1}$. Examples of the statistical measure can include a mean, a median, a mode, a percentile, a quartile, or other central tendency measures.

The comparator circuit 226 can transform one or more second signal portions of the received physiological signal during respective one or more second time windows ($W_{L2}$) into respective one or more historical extreme values ($X_{XR}$) of the physiologic parameter. By way of non-limiting examples, the historical extreme values can include respective maxima or minima of the physiologic parameter using the respective one or more second signal portions during the second time windows $W_{L2}$. In some examples, the historical maxima or the historical minima can be determined from statistical measures evaluated over various sub-portions of each of the second time windows $W_{L2}$, such as running averages over multiple sub-windows within each of the second time windows $W_{L2}$. The sub-windows can be non-overlapped from each other, or at least two of the sub-windows can be overlapped by a specified amount. In an example, the sub-windows of the second time windows $W_{L2}$ can have substantially similar durations as the first time windows $W_{L1}$.

The baseline statistical values $X_{BL}$ and the historical extreme values $X_{XR}$ can represent different reference values of the physiologic parameter when the patient is in a low-risk or risk-free state of developing the target event, such as an event of worsening HF. In an example, the signal input circuit 210 can be configured to sense a thoracic impedance signal. The filter circuit 225 can generate one or more baseline statistical impedance values ($Z_{BL}$) each being a central tendency, or other "smoothing" transformation such as a low-pass filtering, of impedance values measured during the first time window $W_{L1}$. In another example, the signal input circuit 210 can be configured to sense a HS signal. The one or more baseline statistical values can include intensity measures of a HS component such as intensity of S3 heart sound ($\|S3\|_{BL}$), each being a central tendency, or other "smoothing" transformation, of S3 intensity values measured during multiple cardiac cycles within the time window $W_{L1}$. The statistical measure, such as central tendency or smoothing transformation over a relatively long window of $W_{L1}$, may exclude abrupt changes in signal parameter value that may indicate a trend towards worsening HF. As such, the baseline statistical values $X_{BL}$ may represent a low-risk state of the patient developing the target physiologic event.

In an example, the comparator circuit 226 can generate one or more historical extreme impedance values ($Z_{XR}$) each being a maximal impedance value ($Z_{max}$) within a corresponding second time window $W_{L2}$. A larger thoracic impedance may indicate less or reduced thoracic fluid accumulation, hence a lower likelihood for a patient to develop future event of worsening HF. Therefore, the $Z_{max}$ during $W_{L2}$ may represent a historical "risk-free state" where the patient is least likely to develop a future event of worsening HF. In an example, the comparator circuit 226 can generate one or more historical extreme S3 intensity values ($\|S3\|_{XR}$), each being a minimal $\|S3\|$ value ($\|S3\|_{min}$) within a corresponding second time window $W_{L2}$. A prominent S3 may be a sign of congestive HF, while a weaker or reduced S3 intensity may indicate improved compliance of myocardium and less oscillation of blood in the ventricles, hence a lower likelihood for a patient to develop future event of worsening HF. Therefore, the $\|S3\|_{min}$ during $W_{L2}$ may represent a historical "risk-free state" where the patient is least likely to develop a future event of worsening HF. Other physiologic The first time windows $W_{L1}$ used in measuring the baseline statistical values $X_{BL}$ and the respective second time windows $W_{L2}$ used in measuring the historical extreme values $X_{XR}$ can be respectively defined with respect to a reference time $T_{Ref}$, such as the time instant for detecting an event of worsening cardiac condition. In an example, the target physiologic event detector 200 can be configured to detect the target physiologic event regularly or periodically such as on a daily basis, and the $T_{Ref}$ can be progressively shifted such as by one day. In an example, the first time windows $W_{L1}$ can be identical to the respective second time windows $W_{L2}$. In another example, at least one of the first time windows $W_{L1}$ can differ from the respective second time window $W_{L2}$ by at least one of a window start time, a window end time, or a window duration. In an example, at least one of the second time windows $W_{L2}$ can precede the corresponding first time window $W_{L1}$ in time. In another example, at least one of the second time windows $W_{L2}$ can have a longer window duration than the corresponding first time window $W_{L1}$. By way of non-limiting example, the $W_{L1}$ can begin 90 days prior to $T_{Ref}$ and end 60 days prior to $T_{Ref}$, denoted as "90-60 days". Other examples of $W_{L1}$ can include 60-30 days, 80-10 days, 80-20 days, 60-20 days, or 40-20 days prior to $T_{Ref}$. Examples of $W_{L2}$ can include a time duration expires 2 years, 1 year, or 6 months prior to $T_{Ref}$. Examples of measuring the baseline statistical values and the historical extremes values are discussed below, such as with reference to FIG. 4.

The blending circuit 227 can use the one or more baseline statistical values $X_{BL}$ and the respective one or more historical extreme values $X_{XR}$ to generate one or more reference values ($X_{Ref}$) of the physiologic parameter. The reference values $X_{Ref}$ can be a linear or a nonlinear combination of one or more baseline statistical values $\{X_{BL}(i)\}$ each measured during corresponding first time window $\{W_{L1}(i)\}$, and one or more historical extreme values $\{X_{XR}(j)\}$ each measured during corresponding second time windows $\{W_{L2}(j)\}$, that is:

$$X_{Ref} = f(\{X_{BL}(i)\}, \{X_{XR}(j)\}) \qquad (1)$$

where $f$ is a linear or nonlinear function. For example, $X_{Ref}$ can be a weighted sum of N baseline statistical values measured from N first time windows, and M historical extreme values measured from M second windows, that is, $$X_{Ref} = a_1 * X_{BL}(1) + a_2 * X_{BL}(2) + \ldots + a_N * X_{BL}(N) + \\ b_1 * X_{XR}(1) + b_2 * X_{XR}(2) + \ldots + b_N * X_{XR}(M) \qquad (2)$$

where $a_i$ and $b_j$ are weight factors for the respective baseline statistical value $X_{BL}(i)$ and the historical extreme value $X_{XR}(j)$.

In an example, the reference value generator circuit 222 can update one or more of the baseline statistical values $X_{BL}$ using respective one or more specified portions of the received at least one physiological signal. The one or more specified portions can postdate the corresponding one or more first time windows. As a result, the more recent information contained in the physiological signal can be included into the baseline statistical values. In an example, the reference value generator circuit 222 can periodically (such as according to a specified baseline value update frequency), or upon receiving a user's command, update $X_{BL}$ using a linear combination of historically computed $X_{BL}$ and the parameter values obtained from the more recent portions of the physiological signal.

Additionally or alternatively, the reference value generator circuit 222 can initiate a process of updating one or more of the historical extreme values $X_{XR}$ using updated second time windows $W_{L2}$', which may differ from the corresponding second time windows $W_{L2}$ by at least one of a window start time, a window end time, or a window duration. In an example, the reference value generator circuit 222 can update $X_{XR}$ upon receiving a command from a system user, or upon receiving an indication that a specified condition has been fulfilled, such as a detection of an improved cardiac condition. The update of $X_{XR}$ can be less frequent than the update of the $X_{BL}$. In an example, $X_{BL}$ can be updated daily, and $X_{XR}$ can be updated weekly, monthly, quarterly, or yearly.

The short-term value generator circuit 223 can transform one or more third signal portions of the received physiological signal during respective one or more third time windows ($W_S$) into respective one or more short-term values ($X_S$) stored in the memory circuit. In an example, the short-term value generator circuit 223 can generate the one or more short-term values $X_S$ using a statistical measure of the respective one or more second signal portions. Examples of the statistical measures can include a mean, a median, a mode, a percentile, a quartile, or other measures of central tendency measures. In an example, at least some of the third time windows Ws can have shorter window duration than the respective first and second time windows $W_{L1}$ and $W_{L2}$. In an example, the third time windows $W_S$ can be approximately 24 hours, 2-10 days, or 14-28 days in duration. In some examples, some of the first time windows $W_{L1}$ or the second time windows $W_{L2}$ precede the corresponding third time windows $W_S$ in time.

The memory circuit 224 can be coupled to the reference value generator circuit 222, and store one or more of the baseline statistical values $X_{BL}$, the historical extreme values $X_{XR}$, or the reference values $X_{Ref}$ such as produced by the blending circuit 227. The memory circuit 224 can also be coupled to the short-term value generator circuit 223 to store short-term values $X_S$.

The physiologic event detector circuit 230 can be configured to detect a target physiologic event or condition, such as a physiologic event indicative of an onset of a disease, worsening of a disease state, or a change of a disease state. In an example, the physiologic event detector circuit 230 can detect the presence of an event indicative of HF decompensation status, worsening HF, pulmonary edema, pneumonia, or myocardial infarction, among others. In some examples, the physiologic event detector circuit 230 can generate a detection index (DI) using the one or more reference values produced by the reference value generator circuit 222 and the one or more short-term values produced by the short-term value generator circuit 223. In an example, the physiologic event detector circuit 230 can compute the DI using a combination of the differences between the one or more short-term values ($X_S$) and corresponding one or more reference values ($X_{Ref}$), where the differences can be scaled by respective weight factors. The DI can represent the trend of the physiologic parameter over time, such as accumulated deviations from reference values, and can indicate presence or severity of a physiologic condition precipitating a HF decompensation event, such as excessive thoracic fluid accumulation. Examples of computing the DI and using DI to detect a cardiac condition are discussed below, such as with reference to FIG. 3.

The controller circuit 240 can control the operations of the signal input circuit 210, the signal processor circuit 220, the physiologic event detector circuit 230, and the data and instruction flow between these components. In an example, the controller circuit 240 can control the settings of electrical impedance sensing including, for example, selecting electrodes used for current injection and the electrodes used for sensing the resultant voltage, or a beginning and an end of an impedance acquisition and analysis session. In another example, the controller circuit 240 can initiate an impedance acquisition and analysis session in response to a detection of a triggering event such as a change of a physiologic state or a change of the patient's health condition, or a specific time of a day such as in the morning between 6 a.m. and 12 noon. Alternatively, the controller circuit 240 can use an indication of a sleep-to-awake state transition to initiate an impedance acquisition and analysis session for acquiring impedance measurement during specified time following the transition to the awake state.

The user interface unit 250 can be configured to present programming options to the user and receive user's programming input. The user interface unit 250 can include an input device, such as a keyboard, on-screen keyboard, mouse, trackball, touchpad, touch-screen, or other pointing or navigating devices. The input device can enable a system user to program the parameters used for sensing the physiological signals. The user interface can include an output unit that can produce a presentation of information including the detected progression of cardiac condition. The information can be presented in a table, a chart, a diagram, or any other types of textual, tabular, or graphical presentation formats, for displaying to a system user. The presentation of the output information can include audio or other human-perceptible media format to alert the system user of the detected progression of cardiac condition. In an example, at least a portion of the user interface unit 250, such as the user interface, can be implemented in the external system 120.

Figure 3:
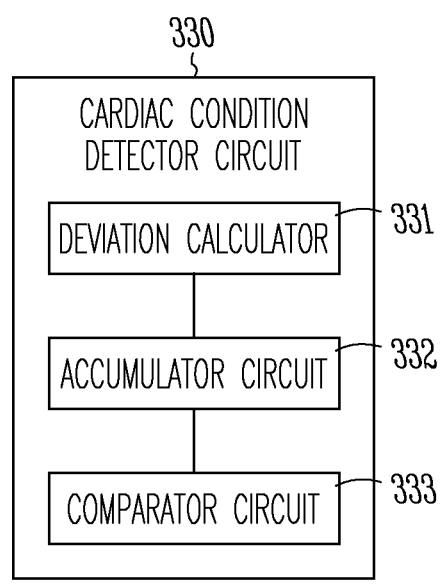
FIG. 3 illustrates generally an example of a cardiac condition detector.

FIG. 3 illustrates generally an example of a cardiac condition detector 330, which can be an example of the physiologic event detector circuit 230 of the target physiologic event detector 200 in FIG. 2. The cardiac condition detector 330 can include one or more of a deviation calculator 331, an accumulator circuit 332, and a comparator circuit 333.

The deviation calculator 331 can be coupled to the reference value generator circuit 222 and the short-term value calculator 227, and configured to compute relative deviations ($\Delta X$) of the one or more short-term values $X_S$, such as provided by the short-term value calculator 227, from the corresponding one or more reference values $X_{Ref}$, such as provided by the reference value generator circuit 222. Examples of the relative deviations can include differences, percentile change, or other relative difference measures. In an example, $\Delta X = X_{Ref} - X_S$. In another example, $\Delta X = (X_{Ref} - X_S)/X_{Ref}$.

The accumulator 332 can compute a detection index (DI) using a combination of at least some of the relative deviations, each scaled by a corresponding weight factor. In an example, the DI can be computed as a weighted sum of the deviations ($\Delta X$), that is, $DI = \sum_{i=1}^{N} \omega_i \cdot \Delta X_i$. When the reference values $X_{Ref}$ is computed using both the baseline statistical values $X_{BL}$ and the historical extreme values $X_{XR}$, the deviation $\Delta X$, such as computed as $\Delta X = X_{Ref} - X_S = f(X_{BL}, X_{XR}) - X_S$, may include information about deviations of $X_S$ from the baseline statistical values $X_{BL}$, and deviations of $X_S$ from the historical extreme values $X_{BL}$. As previously discussed with reference to FIG. 2, the baseline statistical values $X_{BL}$ and the historical extreme values $X_{XR}$ can represent different reference values when the patient is in low-risk or risk-free states of developing the target physiologic event. By incorporating the historical reference values $X_{XR}$ into the reference value $X_{Ref}$, the resultant DI includes information about deviation from the "risk-free state" characterized by $X_{XR}$. For example, a short-term impedance value Zs that is lower than the historical $Z_{max}$, or a short-term S3 intensity $\|S3\|_S$ higher than the historical $\|S3\|_{min}$, may respectively indicate a trend towards an increased risk of developing a future event of worsening HF.

The comparator 333 can compare the DI, such as produced by the accumulator 334, to a criterion such as a threshold value or a specified range. The comparator 333 can generate an indication of detecting a target event such as worsening HF if the DI exceeds the threshold or falls within a specified range. In an example, the DI can be compared to a first threshold to detect an onset of the target event, and compared to a second threshold to detect a termination of the target event. The second threshold can be the same as, or different from, the first threshold. The first and second thresholds can be respectively provided by a system user such as via the user interface unit 250. Alternatively, at least one of the first or second thresholds can be automatically determined as a specified fraction of one of the baseline statistical value $X_{BL}$, the historical extreme value $X_{XR}$ (such as $Z_{Max}$ or $\|S3\|_{Min}$), or the composite reference value $X_{Ref}$. In an example, the first threshold can be a first percentage or fraction of the $X_{BL}$, or the second threshold can be a percentage or a fraction of the $X_{XR}$. Examples of computing the DI using the weighted accumulation are discussed below, such as with reference to FIGS. 4-5.

Figure 4:
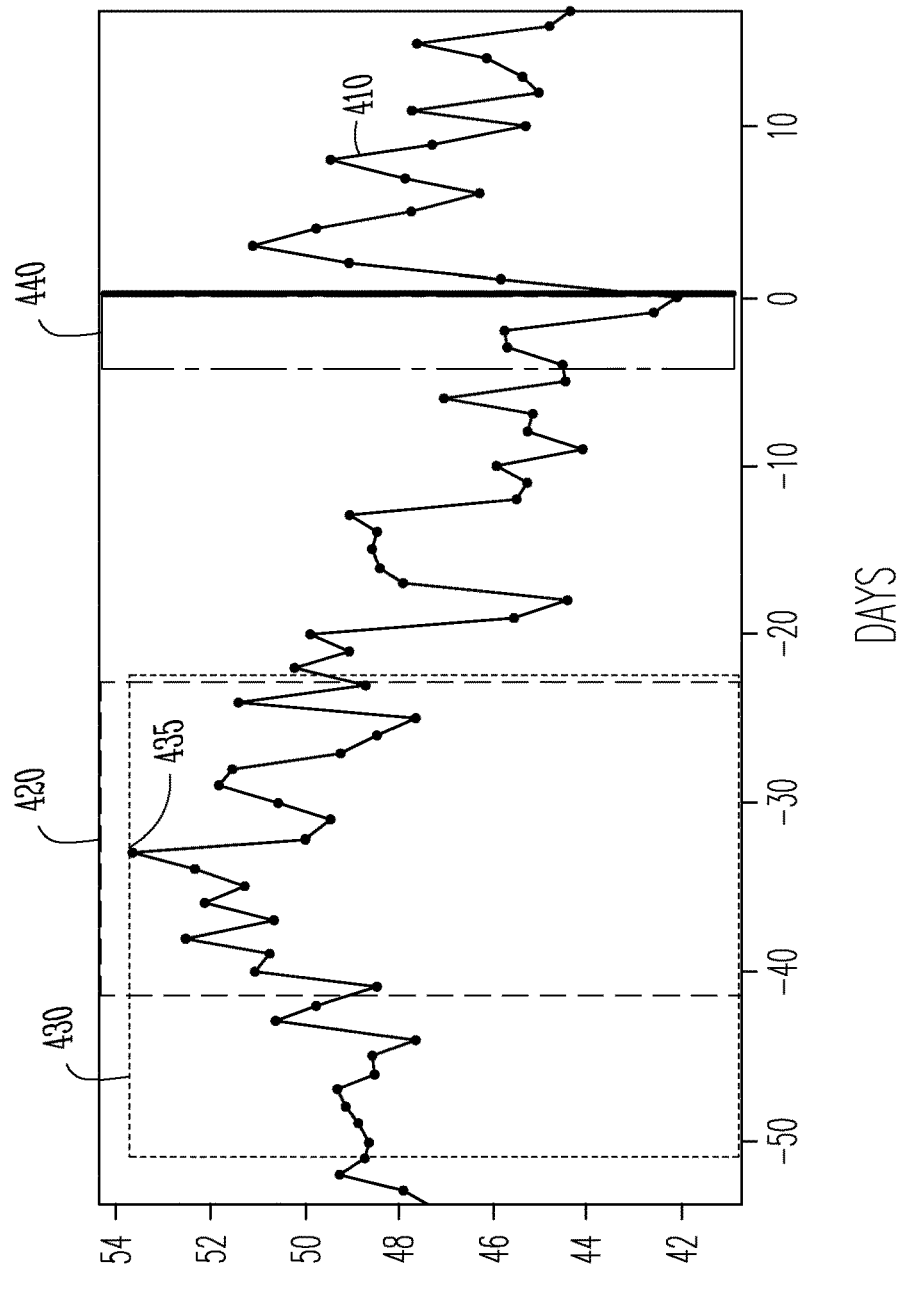
FIG. 4 illustrates generally an example of a trend of impedance measurement over a specified time period.
Figure 5:
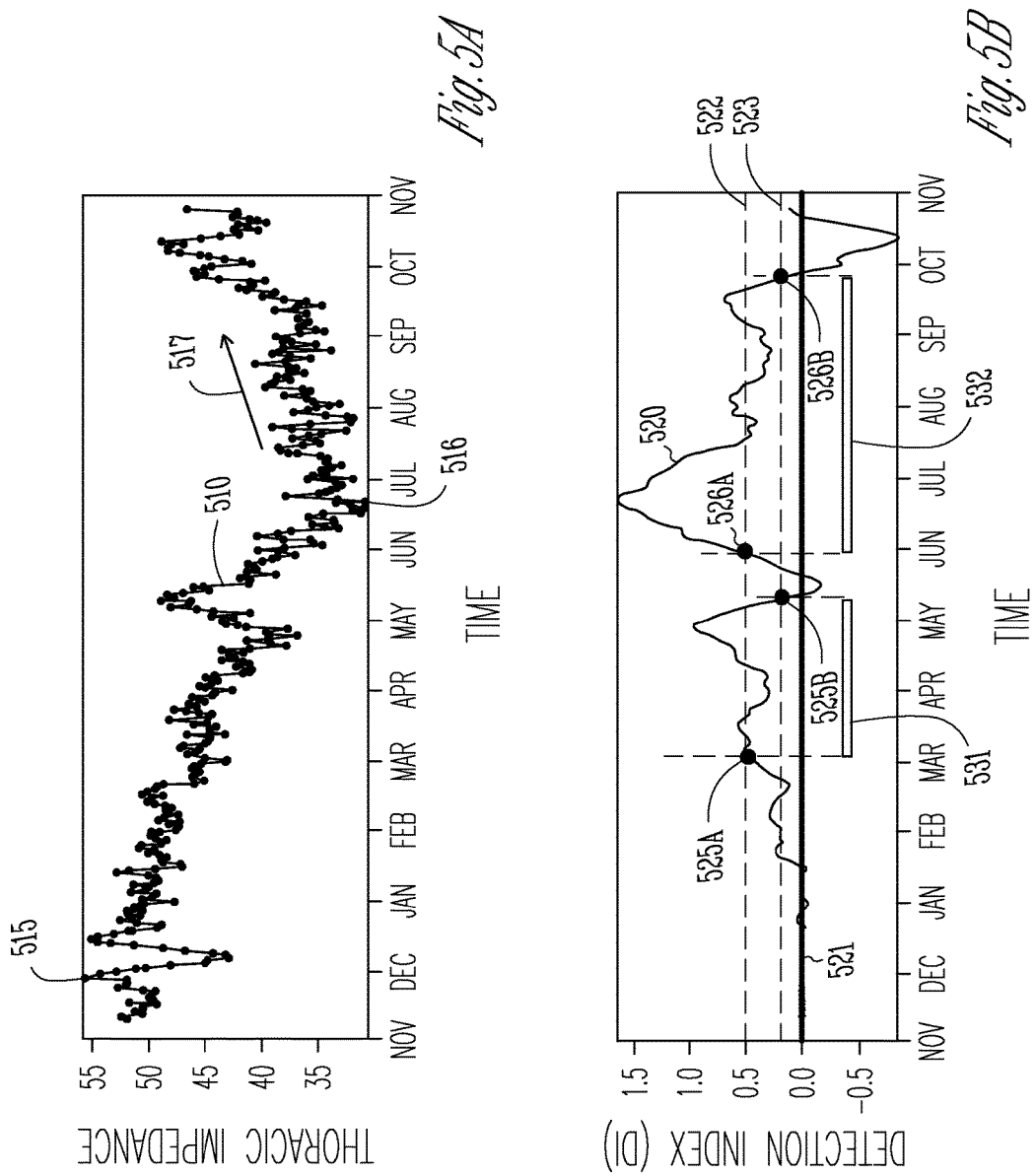
FIGS. 5A-B illustrates generally examples of an impedance trend over a period of time and a trend of detection index (DI) for detecting events of HF decompensation.

FIG. 4 illustrates generally an example of a trend 400 of impedance measurement (as shown on they-axis) calculated over time (as shown on the x-axis), such as over approximately 70 days. The impedance values can be acquired by an impedance sensing circuit, such as the signal input circuit 210, within or communicatively coupled to an implantable medical device (IMD). The impedance sensing circuit can be configured to couple to one or more electrodes on the RV lead and the IMD housing and to acquire measurements from the RV-Can impedance vector ($Z_{RV-Can}$). Each impedance measurement, denoted by data points 410 in the trend 400, represents a characteristic impedance value (such as a median, a mean, or other statistical value) during a 24-hour impedance acquisition and analysis session. The representative impedance value can be generated such as by an impedance sensing circuit coupled to the signal input circuit 210. The impedance signal can be used to detect an event of worsening HF, such as a HF decompensation event.

A first time window 420, a second time window 430, and a short-term time window 440 of the representative impedance values can be respectively defined. The filter circuit 225 can be used to establish a baseline statistical impedance value, $Z_{BL}$, such as a mean or a median of the impedance data within the first time window 420. The comparator circuit 226 can be used to measure a historical extreme impedance value, such as the maximal impedance value $Z_{max}$ at 435, from the impedance data within the second time window 430. In an example, the historical maximal impedance value $Z_{max}$ can be determined from statistical measures evaluated over various sub-portions of the second time window 430. The second window 430 can include multiple sub-windows each having a substantially similar duration as the first window 420. Adjacent sub-windows can be overlapped from each other, and the subsequent sub-window is obtained by forward-shifting the previous sub-window such as by one day. A statistical measure (such as an average impedance) can be computed for each sub-window, and the maximal impedance value $Z_{max}$ can be determined as the maximum of the statistical measures corresponding to some or all of the sub-windows.

The short-term value generator circuit 223A can be used to establish a short-term impedance value Zs, such as a mean or median of the impedance data within the short-term time window 440. The baseline statistical impedance value $Z_{BL}$ and the maximal impedance value $Z_{max}$ can be combined (such as using a weighted sum) at the blending circuit 227 to produce a reference impedance $Z_{Ref}$. A detection decision can be made, such as by the physiologic event detector circuit 230 or the cardiac condition detector circuit 330, when a comparison between the short-term impedance value Zs and the reference impedance value $Z_{Ref}$ meets a specified condition.

FIGS. 5A-B illustrate generally examples of a thoracic impedance (Z) signal and a trend of detection index (DI) for detecting events of HF decompensation. The trend of DI can be used to detect a worsening HF event such as by using the physiologic event detector circuit 230 or any variant thereof, such as the cardiac condition detector circuit 330. The detected worsening HF event can be presented to a system user such as via a display unit in the user interface unit 250

FIG. 5A illustrates an impedance trend 510 that can include representative impedance values (shown on they-axis) over a period of time (shown on the x-axis). The impedance can be sensed according a specified impedance vector that includes one or more electrodes on one or more of the implantable leads such as 108A-C or the can housing 112 implanted or otherwise attached to the patient. A portion of the trend 510 has a time span of approximately 12 months. Each data point in the trend 510 indicates a representative impedance value, which can be computed (such as by the physiologic parameter generator circuit 221) as a mean, a median, or other statistics of impedance measurements during a specified impedance acquisition session, such as a 24-hour session.

The impedance trend 510 reaches its maximal value 515 in an earlier phase of the timeframe shown in FIG. 5A. The impedance subsequently decays until reaching the minimal impedance 516, from which the impedance slowly recovers (increases) as indicated by an upward trend 517. A baseline statistical impedance value $Z_{BL}$ can be computed as a mean, median, or other central tendency measure of impedance measurements within a first long-term time window $W_{L1}$. By way of non-limiting example, the window $W_{L1}$ is defined to be 40 days to 10 days prior to the reference time $T_{Ref}$ at which the DI is to be determined. The baseline statistical impedance value $Z_{BL}$ can be updated periodically using a linear combination of $Z_{BL}$ computed from an old window and the daily impedance value. A historical extreme impedance value, such as a historical maximal impedance value $Z_{Max}$, can be determined using impedance data within a second long-term time window $W_{L2}$. By way of non-limiting example, the window $W_{L2}$ has a duration that expires 12 months prior to $T_{Ref}$. The $W_{L2}$ is therefore long enough to include the maximal impedance 515, which occurs within 12 months until $T_{Ref}$. A composite reference $Z_{Ref}$ can be computed as, for example, a weighted combination of $Z_{BL}$ and $Z_{Max}$. A short-term impedance values $Z_S$ can be computed within one or more short-term time windows each having a duration of, for example, 24 hours.

FIG. 5B illustrates a DI trend 520 indicating DI values (data points on the DI trend 520), as shown on the y-axis, over time as shown on the x-axis. Each DI value can be computed using the physiologic event detector circuit 230 or any variant thereof, such as the cardiac condition detector circuit 330. A deviation ($\Delta Z$) of Zs from the reference $Z_{Ref}$ ($\Delta Z = Z_{Ref} - Z_S$) can be computed, and the DI value can be computed as cumulative deviations over multiple short-term windows. The trend of DI can then be used to detect a worsening HF event. A positive DI value (i.e., above the zero line 521) indicates that accumulatively, the short-term impedance values ($Z_S$) are lower than the reference impedance value ($Z_{Ref}$). Such a decrease in thoracic impedance may indicate an increase in thoracic fluid accumulation, a precursor of worsening HF. Conversely, a negative DI value represents an accumulative increase of $Z_S$ that exceeds the reference $Z_{Ref}$, which may indicate a reduced thoracic fluid, an indication of improved HF status, or termination of a previously detected worsening HF event.

As illustrated in FIG. 5B, the DI trend can be compared to a DI onset threshold 522 to detect an onset of the event of worsening HF, and compared to a DI termination threshold 523 to detect termination of the detected event of worsening HF. A first worsening HF event 531 is detected prior to the impedance reaches minimal value 516, with an onset at 525A when the DI exceeds the DI onset threshold 522 and a termination at 525B when the DI falls below the DI termination threshold 523. Following the minimal value 516A, a second worsening HF event 532 is detected with an onset at 526A when the DI exceeds the DI onset threshold 522, and a termination at 526B when the DI falls below the DI termination threshold 523. The impedance has recovered during this time as indicated by the trend 517, such that the short-term impedance $Z_S$ may exceed the baseline statistical impedance $Z_{BL}$. However, the reference impedance value $Z_{Ref}$ during the impedance recovery phase can be dominated by the historical extreme value $Z_{Max}$ 515. As a result, even though $Z_{BL}$ is lower than $Z_S$, the reference $Z_{Ref}$ may maintain at a level greater than $Z_S$. The deviation $\Delta Z = Z_{Ref} - Z_S$ may still be above the termination threshold 523, such that the second worsening HF event 532 remain to be detected during the impedance recovery period, until the deviation $\Delta Z$ falls below the threshold 523 at 526B.

The DI onset threshold 522 and the DI termination threshold 523 can be automatically determined as a specified fraction of one of the reference value $Z_{Ref}$, the baseline statistical value $Z_{BL}$, or the historical extreme value $Z_{XR}$ (such as $Z_{Max}$). In an example, the DI onset threshold 522 can be based on $Z_{BL}$, and the DI termination threshold 523 can be based on $Z_{Max}$. In an example, as illustrated in FIG. 5B, the DI onset threshold 522 can be higher than the DI termination threshold 523. The detected worsening HF events 531 and 532, including the onset and termination time, can be presented to a system user such as via a display unit in the user interface unit 250.

Figure 6:
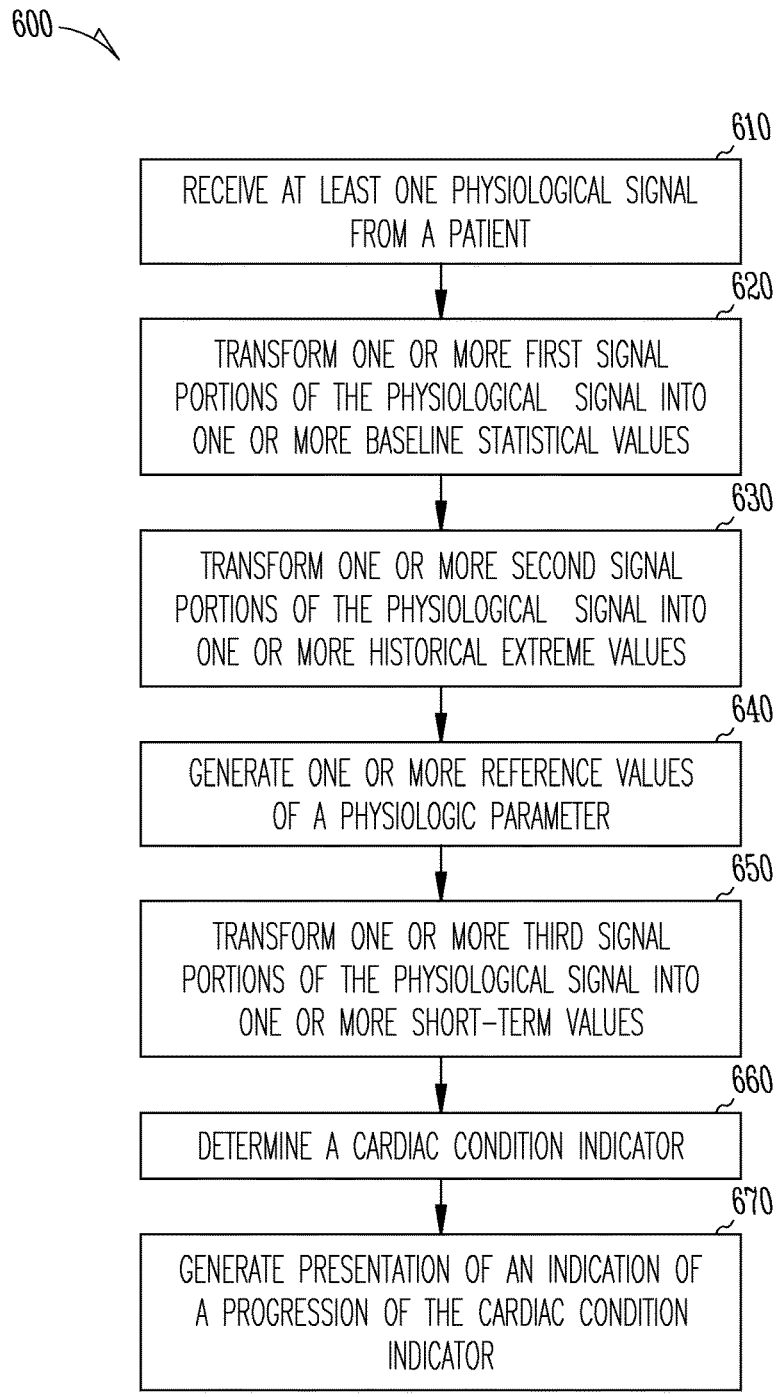
FIG. 6 illustrates generally an example of a method for detecting a target event indicative of progression of cardiac condition in a patient.

FIG. 6 illustrates generally an example of a method 600 for detecting a target event indicative of progression of cardiac condition in a patient. The target event can include a HF decompensation event, an event indicative of worsening HF, or an event indicative of recovery from a HF condition. The method 600 can be implemented and operate in an ambulatory medical device such as an implantable or wearable medical device, or in a remote patient management system. In an example, the IMD 110 or the external system 120, including its various examples discussed in this document, can be programmed to perform method 600, including its various examples discussed in this document.

The method 600 begins at 610 by receiving at least one physiological signal from a patient. Examples of the physiological signal can include one or more of an electrocardiograph (ECG) or electrogram (EGM) such as sensed from electrodes on one or more of the leads 108A-C or the can housing 112, a impedance signal, an arterial pressure signal, a pulmonary artery pressure signal, an RV pressure signal, an LV coronary pressure signal, a coronary blood temperature signal, a blood oxygen saturation signal, a heart sound (HS) signal, or a respiration signal rate signal or a tidal volume signal, among others. In an example, a thoracic or cardiac impedance signal can be sensed according a specified impedance vector that includes one or more electrodes on one or more of the implantable leads such as 108A-C or the can housing 112 implanted or otherwise attached to the patient. The impedance can be sensed in response to a detection of a triggering event such as a change of a physiologic state, a change of the patient's health condition, or a specific time of a day such as when the patient is awake.

The sensed impedance can be pre-processed, including one or more of signal amplification, digitization, filtering, or other signal conditioning operations. One or more statistical or morphological signal metrics can be extracted from the pre-processed signal.

At 620, one or more first signal portions of the received at least one physiological signal during respective one or more first time windows ($W_{L1}$) can be transformed into respective one or more baseline statistical values ($X_{BL}$), such as by using the filter circuit 225. The $X_{BL}$ can be a statistical measure—such as a mean, a median, a mode, a percentile, a quartile, or other central tendency measures—of a physiologic parameter using the respective one or more first signal portions during the one or more first time windows $W_{L1}$. The first time windows $W_{L1}$ can be defined with respect to a reference time $T_{Ref}$, such as the time instant for detecting an event of worsening cardiac condition. Each of the first time windows $W_{L1}$ can be defined by one or more of a window start time, a window end time, and a window duration.

At 630, one or more second signal portions of the received at least one physiological signal during respective one or more second time windows ($W_{L2}$) can be transformed into respective one or more historical extreme values ($X_{XR}$), such as using the comparator circuit 226. By way of non-limiting examples, the $X_{XR}$ can include respective maxima or minima of the physiologic parameter using the respective one or more second signal portions during the one or more second time windows $W_{L2}$. Similar to the $W_{L1}$, the $W_{L2}$ can be defined with respect to a reference time $T_{Ref}$, such as the time instant for detecting an event of worsening cardiac condition. The first time windows $W_{L1}$ can be identical to the respective second time windows $W_{L2}$. Alternatively, at least one of the first time windows $W_{L2}$ can differ from the respective second time window $W_{L2}$ by at least one of a window start time, a window end time, or a window duration. In an example, as illustrated in FIG. 4, at least one of the $W_{L2}$ can precede the corresponding first time window $W_{L1}$ in time, or have a longer window duration than the corresponding first time window $W_{L1}$. The baseline statistical values $X_{BL}$ may represent a low-risk state of the patient developing the target physiologic event.

In an example, the physiological signal received at 610 includes a heart sound (HS) signal, such as sensed by using a HS sensor. One or more baseline statistical values of S3 heart sound intensity ($\|S3\|_{BL}$) can be generated at 620. One or more historical extreme S3 intensity values ($\|S3\|_{XR}$), each being a minimal S311 value ($\|S3\|_{min}$) within a corresponding second time window $W_{L2}$, can be generated at 630. A prominent S3 may be predictive of congestive HF, while a smaller or reduced S3 intensity may indicate improved compliance of myocardium and less oscillation of blood in the ventricles, hence a lower likelihood for a patient to develop future event of worsening HF. In an example, the physiological signal received at 610 includes a thoracic impedance signal. One or more baseline statistical impedance values ($Z_{BL}$) can be generated at 620. One or more historical extreme impedance values ($Z_{XR}$), each being a maximal impedance value ($Z_{max}$) within a corresponding second time window $W_{L2}$, can be generated at 630. A larger thoracic impedance may indicate less or reduced thoracic fluid accumulation, hence a lower likelihood for a patient to develop future event of worsening HF. The $\|S3\|_{min}$ during $W_{L2}$, or the $Z_{max}$ during $W_L$, may represent a historical "risk-free state" where the patient is least likely to develop a future event of worsening HF.

The baseline statistical values $X_{BL}$, or the historical extreme values $X_{XR}$, can be regularly or periodically updated. One or more of the $X_{BL}$ can be updated using respective one or more specified portions of the received at least one physiologic signal, where the one or more specified portions can postdate the corresponding one or more first time windows. One or more of the $X_{XR}$ can be updated using respective one or more updated second time windows, where the one or more updated second time windows differing from the corresponding second time windows by at least one of a window start time, a window end time, or a window duration.

At 640, one or more reference values ($X_{Ref}$) of a physiologic parameter can be generated, such as by using the blending circuit 227, by combining the respective one or more baseline statistical values $X_{BL}$ and the respective one or more historical extreme values $X_{XR}$. The reference values $X_{Ref}$ can be a linear or a nonlinear combination of one or more baseline statistical values $X_{BL}$ and one or more historical extreme values $X_{XR}$.

At 650, one or more third signal portions of the received at least one physiological signal, during respective one or more third time windows ($W_S$), can be transformed into respective one or more short-term values ($X_S$). The one or more third time windows can be shorter than the respective first and second time windows. In an example, at least some of the third time windows $W_S$ can have shorter window duration than the respective first and second time windows $W_{L1}$ and $W_{L2}$. In some examples, some of the first time windows $W_{L1}$ or the second time windows $W_{L2}$ precede the corresponding third time windows Ws in time.

At 660, a cardiac condition indicator can be produced using the one or more short-term values ($X_S$) and the one or more reference values ($X_{Ref}$). The cardiac condition indicator can indicate presence of an event indicative of HF decompensation status, worsening HF, pulmonary edema, pneumonia, or myocardial infarction, among others. In an example, the cardiac condition indicator can be computed as a combination of the differences between the one or more short-term values ($X_S$) and corresponding one or more reference values ($X_{Ref}$), where the differences can be scaled by respective weight factors. In an example, the cardiac condition indicator can be computed as accumulation of deviations of the short-term thoracic impedance values ($Z_S$) from the reference impedance values ($Z_{Ref}$), and can indicate presence or severity of a physiologic condition precipitating a HF decompensation event, such as excessive thoracic fluid accumulation. A target cardiac condition, such as worsening HF, is deemed detected if the cardiac condition indicator exceeds the threshold or falls within a specified range.

At 670, information including the detection of the progression of cardiac condition indicator can be presented to the system user in a human-perceptible format in an output unit, such as a display or a user interface unit 250. In an example, the output information can be presented in a table, a chart, a diagram, or any other types of textual, tabular, or graphical presentation formats. In an example, an alert can be produced if a worsening HF is detected. The alert can be in audio or other human-perceptible media format. The method 600 can additionally include delivering a therapy, such as electrostimulation therapy delivered to the heart, a nerve tissue, or other target tissues in response to the detection of a worsening HF event.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
a signal input circuit configured to receive at least one physiological signal from a patient;
a signal processor circuit, including:
a memory circuit;
a reference value generator circuit including:
a filter circuit to transform one or more first signal portions of the received at least one physiological signal during respective one or more first time windows into respective one or more baseline statistical values;
a comparator circuit to transform one or more second signal portions of the received at least one physiological signal during respective one or more second time windows into respective one or more historical extreme values; and
a blending circuit to generate one or more reference values of a physiologic parameter stored in the memory circuit using the respective one or more baseline statistical values and the respective one or more historical extreme values; and
a short-term value generator circuit configured to transform one or more third signal portions of the received at least one physiological signal during respective one or more third time windows into respective one or more short-term values stored in the memory circuit, the one or more third time windows shorter than the respective first and second time windows;
a cardiac condition detector circuit configured to determine a cardiac condition indicator using the one or more short-term values and the one or more reference values; and
an output unit, configured to generate a human-perceptible presentation of an indication of a progression over time of the cardiac condition indicator.

2. The system of claim 1, wherein:
the filter circuit is configured to produce the one or more baseline statistical values including respective statistical measures of the physiologic parameter using the respective one or more first signal portions; and
the comparator circuit is configured to produce the one or more historical extreme values including respective one or more maxima or minima of the physiologic parameter using the respective one or more second signal portions.

3. The system of claim 1, wherein the one or more first time windows are different from the respective one or more second time windows by at least one of a window start time, a window end time, or a window duration.

4. The system of claim 3, wherein at least one of the one or more second time windows precedes the corresponding first time window in time.

5. The system of claim 3, wherein at least one of the one or more second time windows has a longer window duration than the corresponding first time window.

6. The system of claim 1, wherein:
the signal input circuit is configured to receive the at least one physiologic signal including a heart sound (HS) signal;
the filter circuit is configured to generate the one or more baseline statistical values including central tendency of S3 heart sound intensity values using one or more first signal portions of the received HS signal; and
the comparator circuit is configured to generate the one or more historical extreme values including minimal S3 heart sound intensity values using one or more second signal portions of the received HS signal.

7. The system of claim 1, wherein:
the signal input circuit is configured to receive the at least one physiologic signal including an impedance (Z) signal;
the filter circuit is configured to generate the one or more baseline statistical values including central tendency of Z values using one or more first signal portions of the received Z signal; and
the comparator circuit is configured to generate the one or more historical extreme values including maximal Z values using one or more second signal portions of the received Z signal.

8. The system of claim 1, wherein the reference value generator circuit is further configured to update the one or more reference values, including one or more of:
update the one or more baseline statistical values using respective one or more specified portions of the received at least one physiologic signal, the one or more specified portions postdate the corresponding one or more first time windows; or
update the one or more historical extreme values using respective one or more updated second time windows, the one or more updated second time windows differing from the corresponding second time windows by at least one of a window start time, a window end time, or a window duration.

9. The system of claim 1, wherein the short-term value generator circuit is configured to generate the one or more short-term values using a statistical measure of the respective one or more third signal portions of the received at least one physiological signal.

10. The system of claim 1, wherein the cardiac condition detector circuit is configured to determine the cardiac condition indicator using a combination of differences between the one or more short-term values and the corresponding one or more reference values, each of the differences scaled by a specified weight factor.

11. The system of claim 1, wherein the cardiac condition detector circuit is configured to detect an onset of a cardiac condition when a cardiac condition indicator meets a first criterion, and to detect a termination of the cardiac condition when the cardiac condition indicator meets a second criterion.

12. A method, comprising:
receiving at least one physiological signal sensed from a patient using a signal input circuit;
transforming one or more first signal portions of the received at least one physiological signal during respective one or more first time windows into respective one or more baseline statistical values using a filter circuit in a reference value generator circuit of a signal processor circuit;
transforming one or more second signal portions of the received at least one physiological signal during respective one or more second time windows into respective one or more historical extreme values using a comparator circuit in the reference value generator circuit;
generating one or more reference values of a physiologic parameter stored in a memory circuit using the respective one or more baseline statistical values and the respective one or more historical extreme values using a blending circuit in the reference value generator circuit;

transforming one or more third signal portions of the received at least one physiological signal during respective one or more third time windows into respective one or more short-term values stored in the memory circuit using a short-term value generator circuit of the signal processor circuit, the one or more third time windows shorter than the respective first and second time windows;

determining a cardiac condition indicator using the one or more short-term values and the one or more reference values using a cardiac condition detector circuit; and generating a human-perceptible presentation of an indication of a progression over time of the cardiac condition indicator using an output unit.

13. The method of claim 12, wherein the one or more baseline statistical values include respective statistical measures of the physiologic parameter using the respective one or more first signal portions, and the one or more historical extreme values including respective one or more maxima or minima of the physiologic parameter using the respective one or more second signal portions.

14. The method of claim 12, wherein the one or more first time windows are different from the respective one or more second time windows by at least one of a window start time, a window end time, or a window duration.

15. The method of claim 12, wherein:
receiving the at least one physiological signal includes receiving a heart sound (HS) signal;
transforming the one or more first signal portions includes computing central tendency of S3 heart sound intensity values using one or more first signal portions of the received HS signal; and
transforming the one or more second signal portions includes identifying one or more minimal S3 heart sound intensity values from respective one or more second signal portions of the received HS signal.

16. The method of claim 12, wherein:
receiving the at least one physiological signal includes receiving an impedance (Z) signal;
transforming the one or more first signal portions includes computing central tendency of Z values using one or more first signal portions of the received Z signal; and
transforming the one or more second signal portions includes identifying one or more maximal Z values from respective one or more second signal portions of the received Z signal.

17. The method of claim 12, further comprising one or more of:
updating the one or more baseline statistical values using respective one or more specified portions of the received at least one physiologic signal, the one or more specified portions postdate the corresponding one or more first time windows; or
updating the one or more historical extreme values using respective one or more updated second time windows, the one or more updated second time windows differing from the corresponding second time windows by at least one of a window start time, a window end time, or a window duration.

18. The method of claim 12, wherein determining the cardiac condition indicator includes determining a combination of differences between the one or more short-term values and the corresponding one or more reference values, each of the differences scaled by a specified weight factor.

19. The method of claim 12, wherein the one or more short-term values include a statistical measure of the respective one or more third signal portions of the received at least one physiological signal.

20. The method of claim 12, comprising detecting an onset of a cardiac condition using the cardiac condition detector circuit when a cardiac condition indicator meets a first criterion, and detecting a termination of the cardiac condition using the cardiac condition detector circuit when the cardiac condition indicator meets a second criterion.

* * * * *